United States Patent [19]

Yock

[11] Patent Number: 4,794,931
[45] Date of Patent: Jan. 3, 1989

[54] CATHETER APPARATUS, SYSTEM AND METHOD FOR INTRAVASCULAR TWO-DIMENSIONAL ULTRASONOGRAPHY

[75] Inventor: Paul G. Yock, Menlo Park, Calif.

[73] Assignee: Cardiovascular Imaging Systems, Inc., Mountain View, Calif.

[21] Appl. No.: 834,893

[22] Filed: Feb. 28, 1986

[51] Int. Cl.[4] .............................................. A61B 10/00
[52] U.S. Cl. ........................ 128/660.03; 128/662.06; 128/305
[58] Field of Search ............... 128/660, 661, 663, 4–6, 128/303.1, 305, 303.15, 303.17

[56] References Cited

U.S. PATENT DOCUMENTS

| 3,817,089 | 6/1974 | Eggleton et al. | 128/661 X |
| 3,938,502 | 2/1976 | Bom | 128/661 X |
| 3,942,530 | 3/1976 | Northened | 128/303.15 |
| 4,020,847 | 5/1977 | Clark, III | 128/305 |
| 4,275,597 | 6/1981 | Quedens et al. | 128/660 X |
| 4,466,443 | 8/1984 | Utsugi | 128/660 |
| 4,475,553 | 10/1984 | Yamaguchi et al. | 128/660 |
| 4,572,203 | 2/1986 | Feinstein | 128/661 |
| 4,576,177 | 3/1986 | Webster, Jr. | 128/660 |
| 4,587,972 | 5/1986 | Morantle, Jr. | 128/660 |
| 4,633,882 | 1/1987 | Matsuo et al. | 128/660 |
| 4,669,469 | 6/1987 | Gifford, III et al. | 128/305 |

FOREIGN PATENT DOCUMENTS 2424733  1/1980  France ..................... 128/4

OTHER PUBLICATIONS

Garrett, L. "A Catheter Assembly", PCT Appln. No. PCT/US82/01669 Published as WO83/01893 on Jun. 9, 1983.
Simpson, J. B. "Atherectomy Device & Method", Europ. Patent Appln. No. 0 163 502 Publ. 04.12.85.

Primary Examiner—Francis J. Jaworski
Attorney, Agent, or Firm—Flehr, Hohbach, Test, Albritton & Herbert

[57] ABSTRACT

Ultrasonic apparatus, system and method for high resolution intravascular imaging to assist indovascular lesions and to monitor the results of interventional therapy. An ultrasonic transducer is carried by the distal end of a catheter adapted for insertion into a vessel, and either the transducer or another element is rotated and/or translated relative to the catheter to image different portions of the vessel.

28 Claims, 3 Drawing Sheets

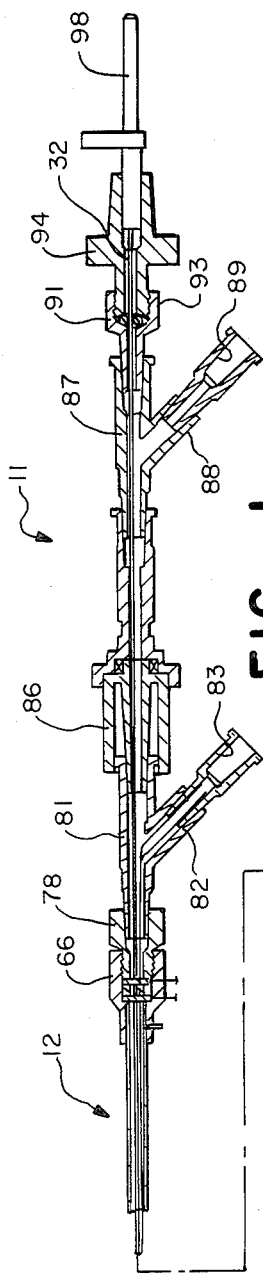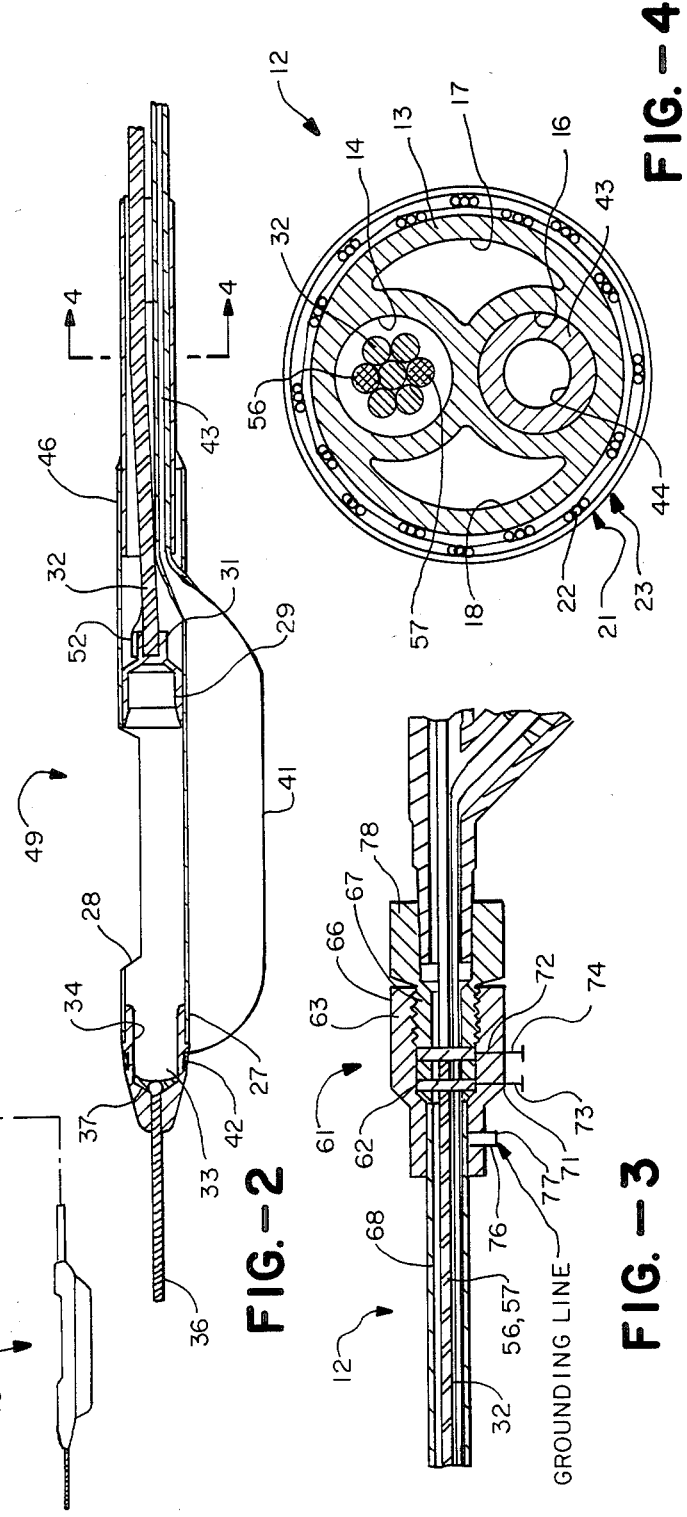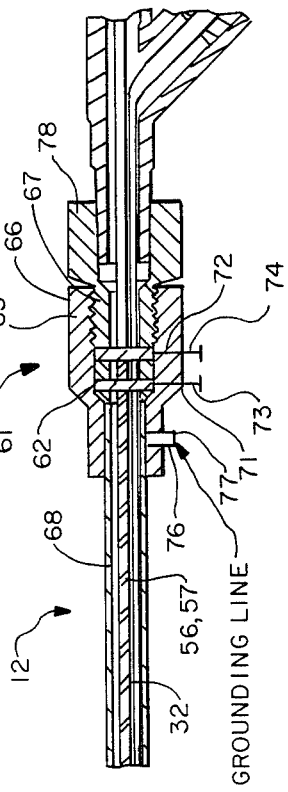

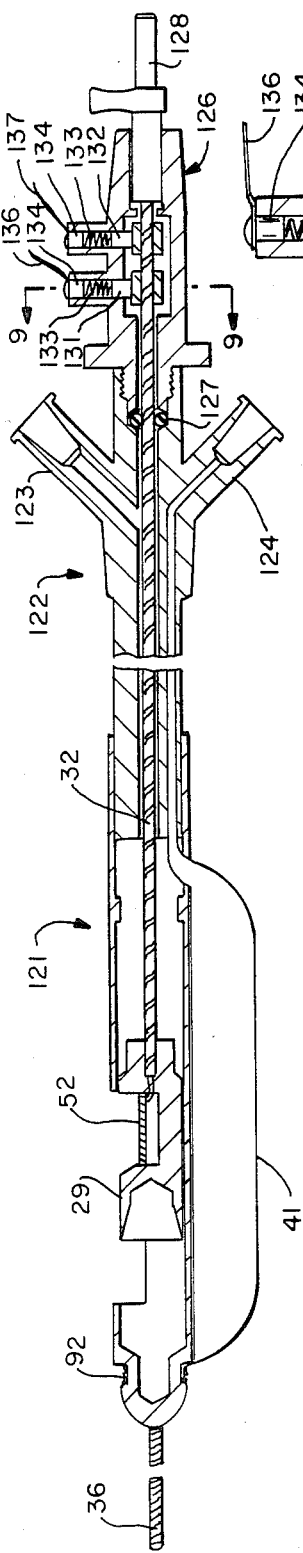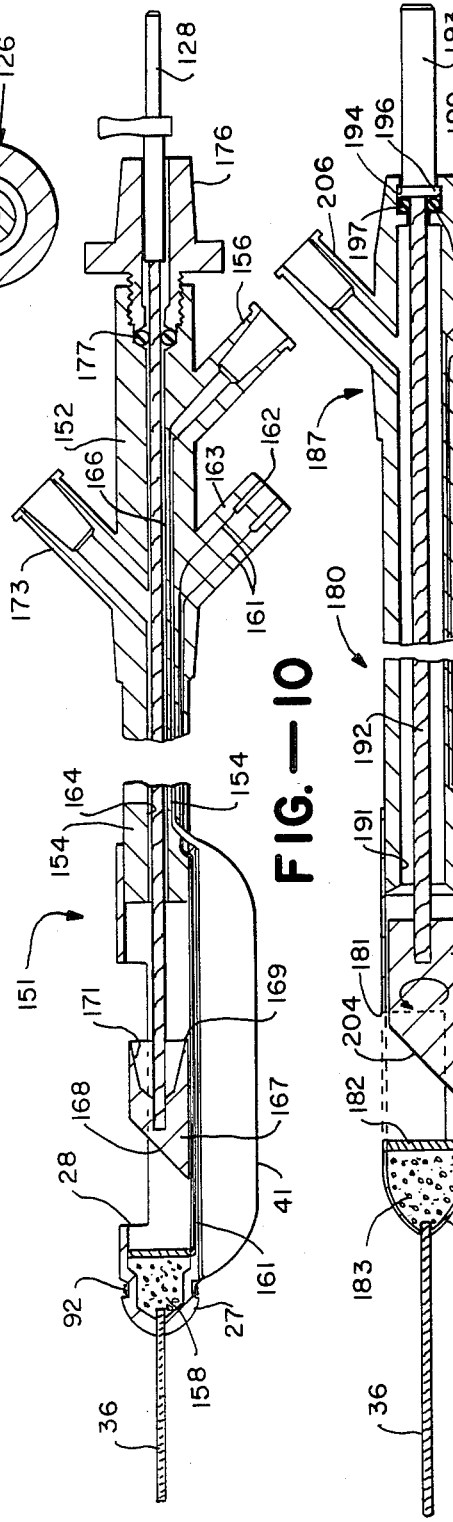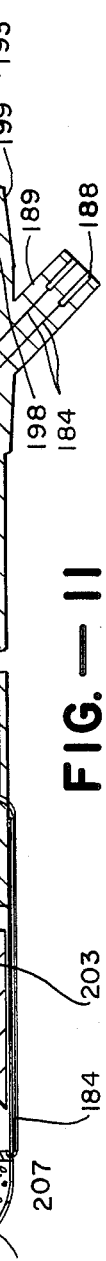

CATHETER APPARATUS, SYSTEM AND METHOD FOR INTRAVASCULAR TWO-DIMENSIONAL ULTRASONOGRAPHY

This invention relates to a catheter apparatus, system and method for intravascular two-dimensional ultrasonography and more particularly to such an apparatus, system and method for providing high resolution imaging for assessing endovascular lesions and for monitoring the results of interventional therapy.

Ultrasonic two-dimensional imaging apparatus and systems have heretofore been provided for use in endoscopy for examining the gastrointestinal tract. Such a device is disclosed in U.S. Pat. No. 4,494,549.

Such devices have been relatively large and inflexible and are completely unsuitable for use in connection with the vascular system of the human body. In addition there is no provision for guiding such devices into specific branches of blood vessels. There is therefore a need for a new and improved catheter apparatus, system and method which can be utilized for performing intravascular two-dimension ultrasonography.

In general, it is an object of the present invention to provide a catheter apparatus, system and method for intravascular two-dimensional ultrasonography.

Another object of the invention is to provide an apparatus, system and method of the above character which has a high resolution capability.

Another object of the invention is to provide an apparatus, system and method of the above character which can be utilized for assessing endovascular lesions.

Another object of the invention is to provide an apparatus, system and method of the above character which can be utilized for monitoring the results of interventional therapy.

Another object of the invention is to provide an apparatus, system and method of the above character which can be used with atherectomy devices.

Another object is to provide an apparatus, system and method capable of selective cannulation of branch vessels.

Additional objects and features of the invention will appear from the following description in which the preferred embodiments are set forth in detail in conjunction with the accompanying drawings.

FIG. 1 is a side elevational view partially in cross section of a catheter apparatus incorporating the present invention.

FIG. 2 is an enlarged cross sectional view of the distal extremity of the apparatus shown in FIG. 1.

FIG. 3 is an enlarged cross sectional view of an intermediate portion of the apparatus shown in FIG. 1.

FIG. 4 is an enlarged cross sectional view taken along the line 4—4 of FIG. 1.

FIG. 8 is an enlarged cross-sectional view of another embodiment of a catheter apparatus incorporating the present invention.

FIG. 9 is a cross-sectional view taken along the lines 9—9 of FIG. 8.

FIG. 10 is an enlarged cross-sectional view of still another embodiment of a catheter apparatus incorporating the present invention.

FIG. 11 is an enlarged cross-sectional view of another embodiment of the catheter apparatus incorporating the present invention.

Figure 5:
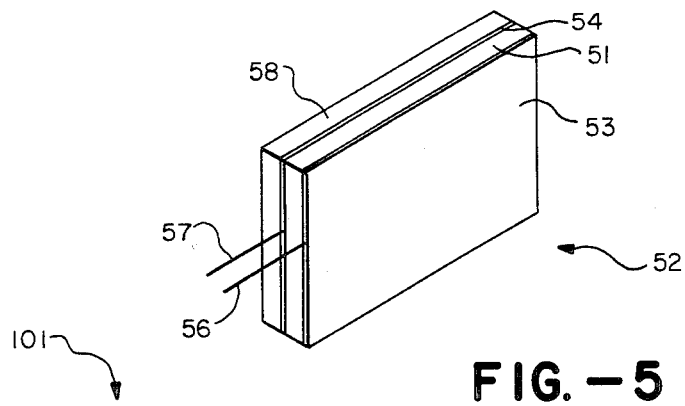
FIG. 5 is an isometric view of the crystal assembly which forms a part of the apparatus shown in FIG. 1.

In general the catheter apparatus of the present invention consists of a flexible tubular element which is adapted to be inserted into a vessel in the vascular system. A flexible rotatable elongate element is disposed in the tubular element. An ultrasonic transducer is carried by the flexible tubular element. Electrical circuitry is carried by the flexible tubular element and is connected to the ultrasonic transducer for supplying signals to and receiving signals from the transducer. In the system, a transmitter is provided for supplying signals to the ultrasonic transducer and a receiver is provided for receiving signals from the ultrasonic transducer. A motor is provided for rotating the flexible elongate element. Timing and control circuitry is provided for controlling the operation of the motor and the transmitter and receiver. A display is provided which is operated under the control of the timing and control circuitry for displaying the image information which is received by the receiver.

More in particular, the catheter apparatus 11 of the present invention consists of an elongate tubular assembly 12. The elongate tubular assembly 12 consists of an elongate tubular element 13 which is provided with four lumens 14, 16, 17 and 18 with the lumen 14 serving as a torque tube, lumen 16 serving as a balloon tube and lumens 17 and 18 serving as infusion tubes or lumens as hereinafter described. As can be seen the tubular element 13 is formed of a single extrusion which provides the four lumens with the lumens 14 and 16 being substantially circular in cross section and the lumens 17 and 18 being arcuate in shape with the configuration of each being determined by three arcs with one of the arcs being concentric with the outer diameter of the tubular element 13 and with the two smaller arcs being concentric with the lumens 14 and 16 respectively.

A braided shield 21 is provided on the exterior of the tubular element 13 and takes the form of one or more layers of braided strands 22 formed of a suitable magnetic material such as stainless steel strands. The shield 21 serves as an electrical shield. A cover tube 23 covers the braided shield 21 and extends the length of the tubular element 13. The cover tube 23 can be formed of a suitable material such as a heat shrinkable plastic which is shrunk tightly onto the braided shield 21 and provides a smooth outer surface so that the tubular assembly 12 can readily enter a vessel of the vascular system of a patient.

A work performing device such as an atherectomy or cutting device disclosed in U.S. patent application Ser. No. 732,691 filed on May 10, 1985 European Patent Application Publication No. 0 163 502 published Dec. 4, 1985 is secured to the distal extremity of the tubular assembly 12. This cutting device 26 is described in said co-pending application and consists of a housing 27 which is provided with a cut-out 28. A rotary cutter 29 is rotatably disposed within the housing 27 and is provided with a hub 31 that is secured to a flexible rotatable torque cable 32. The cable 32 is disposed in and extends through the torque tube lumen 14. The torque cable 32 is formed of a suitable material such as stainless steel. The housing 27 is provided with a rounded tip 33 having a recess 34 which is adapted to receive material which is removed by the rotary cutter 29 as the cutter 29 is advanced as hereinafter described. A spring tip guide or guide wire 36 capable of being shaped is secured to the rounded tip 33 and extends forwardly therefrom and serves to guide or steer the housing 27 as the tubular assembly 12 with the cutting device 26 secured thereto is introduced into the vessel of the vascular system of the patient. As shown, the spring tip guide 36 can be secured to the rounded tip 33 by suitable means such as solder 37. It thus can be seen that the guide wire 36 is associated with the housing 27. Alternatively a movable guide wire can be carried by the housing for facilitating steering of the housing into the desired vessel of the patient.

A balloon 41 of an expandable type is secured to the housing in a region opposite the cutout 28 and has its distal extremity bonded around the tip 33 by suitable means such as an adhesive 42. As shown in FIG. 2, the balloon 41 underlies substantially the entire length of the housing 27. The balloon 41 is in communication with a balloon tube 43 which extends through the balloon tube lumen 16 in the tubular element 13. The balloon tube 43 is provided with a lumen 44 through which a medium can be introduced for inflating the balloon 41 and removed for deflating the balloon 41. The proximal extremity of the balloon 41 and the proximal extremity of the housing 27 is secured to the distal extremity of the tubular assembly 12 by suitable means such as heat shrinkable tubing 46.

Means is provided for imaging the region in which the work performing device 26 is located and in this particular case, with the present invention takes the form of a two-dimensional ultrasound image system 49. The system 49 includes a single crystal 51 (see FIG. 5) which is mounted on the hub 31 and is secured thereto by suitable means such as an adhesive. The crystal 51 is part of an assembly 52. The crystal 51 should be capable of operating at a frequency range of 5 to 50 megahertz and typically can be formed of a suitable material such as barium titanate or cinnabar. As can be seen from FIG. 5, the crystal 51 has a rectangular block-like configuration and has two opposed surfaces covered by metallic conducting films 53 and 54 formed of a suitable material such as chrome or gold. The material of the films can be formed of a foil or can be in the form of films evaporated or sputtered onto the opposite surfaces of the crystal 51. The films 53 and 54 serve as electrodes and are connected to connecting wires 56 and 57 by suitable means such as solder. Means is provided for damping out the oscillations from the backside of the crystal 51 and takes the form of a rectangular block 58 formed of a suitable backing material. This backing material can be formed in a conventional manner so as to cancel out oscillations from the side of a crystal in which the backing material is disposed.

The wires 56 and 57 are braided onto the torque cable 32 and rotate with the torque cable. The wires 56 and 57 extend towards the proximal extremity of the tubular assembly 12 and extend into a fitting 61 (see FIG. 3) formed of a suitable material such as plastic. A pair of spaced apart slip rings 62 and 63 formed of a conducting material such as copper are secured to the torque cable 32. The wire 56 is bonded to the slip ring 62 and the wire 57 is bonded to the slip ring 63. A fitting 66 is provided which has a threaded bore 67. The tubular assembly 12 extends through the fitting 66 and a reinforcing sleeve 68 extends over the portion of the tubular assembly 12 extending therethrough. A pair of spring urged contacts 71 and 72 are carried by the fitting 66 and are adapted to slidably engage the slip rings 62 and 63. The contacts 71 and 72 are connected to conductors 73 and 74. A grounding lug 76 is provided on the fitting 66 and makes electrical contact with the braided shield 21. A conductor 77 is connected to the grounding lug 76.

Figure 6:
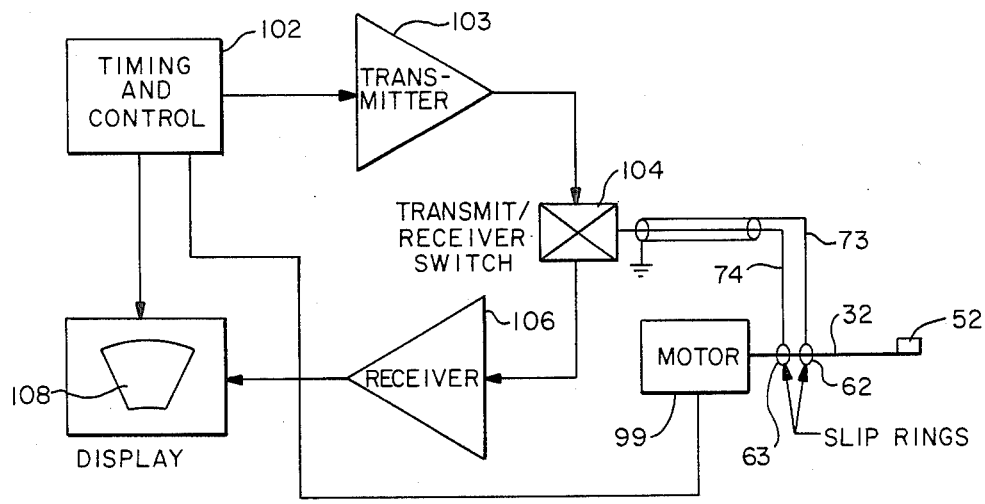
FIG. 6 is a schematic block diagram of the electrical and electronic apparatus utilized in the system.

A male fitting 78 (see FIG. 1) is threaded into the threaded bore 67. A single arm adapter 81 is mounted in the male fitting 78 and carries an arm 82 having thereon a balloon inflation port 83 that is in communication with the lumen 44 in the balloon tube 43 disposed in the tubular assembly 12. The single arm adapter 81 is secured to a rotating adapter 86 of a conventional type and through which the tubular assembly 12 extends. Another single arm adapter 87 is mounted in the rotating adapter and is provided with a side arm 88 having an infusion port 89 disposed therein which is in communication with the infusion lumens 17 and 18 provided in the tubular assembly 12. A tapered fitting 91 is mounted in the single arm adapter 87 and is provided with a threaded bore 92 which carries an O-ring 93 that is adapted to be engaged by a male type fitting 94 to form a liquid-tight seal between the tubular assembly 12 and the torque cable 32 which extends therethrough. The torque cable 32 is secured to a suitable drive member such as a clutch member 98 of the type described in co-pending application Ser. No. 732,691 filed on May 10, 1985 and as also described in application Ser. No. 031,168, filed Mar. 25, 1987, which is a file wrapper continuation of Ser. No. 834,743, filed Feb. 28, 1986, now abandoned. As described in said co-pending applications, the clutch member 98 is adapted to be secured to motive drive means of the type described therein consisting of a motor drive unit which in the present application is identified as a motor 99 (see FIG. 6). The motor 99 is driven by and is under the control of electronic circuitry forming a part of system 49. The part of the system 49 shown in block diagram form is substantially conventional and can be of a suitable type such as certain equipment identified as Model 851B manufactured by Advanced Technology Laboratories, Inc. of Bothel, Wash. As shown in FIG. 6, such apparatus includes a timing and control block 102 which supplies pulses to a transmitter 103. The output of the transmitter 103 is supplied through a transmit receive switch 104 which supplies the signals on the conductors 73 and 74 through the slip rings 62 and 63 onto the conductors 56 and 57 connected to the crystal 51. During the time that the transmitter 103 is supplying high frequency energy to the crystal, the crystal 52 is being rotated by the motor driving the torque cable 32 with the motor 99 being under the control of the timing and control block 102. The motor 99 is of a type such as an open loop stepping motor or a closed drop servo controlled motor which can be driven by the timing and control block 102.

Figure 7:
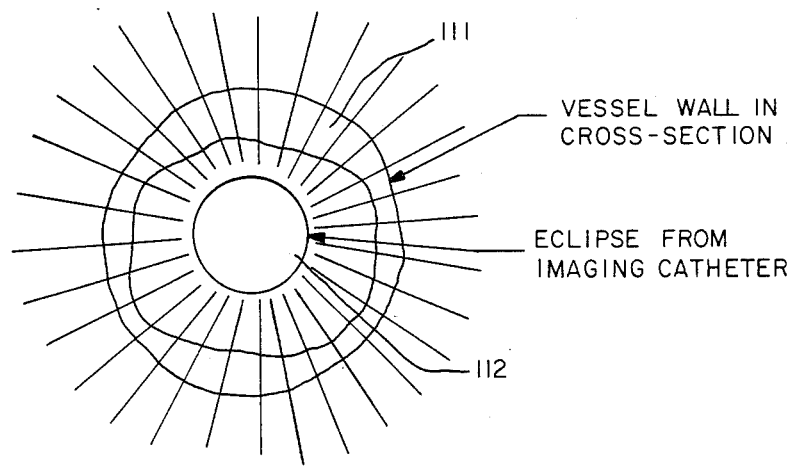
FIG. 7 is a two dimension display of an ultrasonogram which can be obtained with the apparatus and system shown in FIGS. 1-6.

The transmitter generates a high voltage pulse in the 100 to 300 volt range for excitation of the transducer crystal 51. Supplying high voltage pulses to the crystal causes the transducer to produce sonic waves which emanate therefrom into the surrounding tissue structure. Portions of the sonic energy wave reflected by the tissue structure back to the transducer and the transducer 51 acts as a receiver and picks up the sonic vibrations and converts them into electrical signals which are supplied by the conducting wires 56 and 57 back to the slip rings 62 and 63 through the conductors 73 and 74 and through the transmit receive switch 104 to a receiver 106. These signals are amplified and supplied to a display unit 107 which includes a CRT screen 108 under the control of the timing and control block 102 to supply an image 109 on the display 108 which can be of the type shown in FIG. 7. As can be seen from FIG. 7, as viewed through 360°, the vessel wall 111 of the image 109 is shown as indicated having different cross sections depending upon the build-up of plaque therein. A central region 112 of the image is eclipsed because of the imaging catheter. Alternatively, if desired only a sector of a lesser angle than 360° can be viewed.

The catheter apparatus of the present invention can be constructed in various sizes. For example, in a 9 French size, the balloon can have a length of approximately 100 millimeters and a diameter of approximately 3 millimeters (9 French). Sizes down to 3 French can be accomplished with the construction of the present invention.

Operation and use of the catheter apparatus, system and method during intravascular ultrasonography can now be briefly described as follows. Let it be assumed that it is desired to utilize the apparatus, system and method of the present invention to remove the atheroma in a blood vessel of a patient. The catheter of the catheter apparatus of the present invention is introduced into a vessel of the patient as, for example, into the femoral artery and introducing the catheter into the artery by the use of the guide wire 36. The progress of the catheter into the vessel of the patient can be observed under x-ray fluoroscopy. As soon as the cutting device has entered into a region which is desired to remove certain material from the vessel and before a cutting operation is commenced, the atheroma itself can be viewed by operation of the ultrasonic imaging system 49. This can be accomplished by operating the timing control block 102 to cause operation of the motor 99 which in turn causes rotation of the torque cable 32 and the crystal assembly 52 to scan the interior of the vessel in which the crystal 51 is disposed. An image of what is being scanned will appear on the screen 108 of the display device 107. During the time this rotary scanning is taking place, the cable 32 can be advanced to advance the cutter so that the entire region in which the material is to be removed can be scanned. After the scan, the cable 32 can be retracted slightly so that the proximal extremity of the cutout 28 lies at the proximal extremity of the atheroma. In order to stabilize the cutting device, the balloon 41 can be inflated so as to urge the cutout 28 of the housing 27 towards the portion of the atheroma it is desired to remove. The motor 99 can then be energized to rotate the cutter 29. As the cutter 29 is rotated, it can be advanced to progressively remove the material which is disposed within the cutout 28 of the housing 27. As this material is removed it is pushed forwardly and eventually moves into the recess 34. The balloon 41 can then be deflated and the catheter apparatus removed from the vessel after which the material which has been deposited in the recess 34 can be removed and the cutting device cleaned for reinsertion into the vessel of the patient for removal of additional material from the vessel if required.

During the time that the cutting operation is taking place, the cutting operation can be viewed ultrasonically by the rotating crystal 51 which places an image on the screen 108. From this image it can be ascertained how well the cutter is performing in removing the material and whether or not an additional pass of the cutter is required. It should be appreciated that if necessary several passes of the cutter can be made and if necessary, the catheter assembly can be removed from the vessel of the patient to clean out material which has been removed and deposited in a recess 34.

Another embodiment of the catheter apparatus of the present invention is shown in FIG. 8. Many of the parts are very similar to the parts utilized in the embodiment of the invention shown in FIG. 1 and have been given the corresponding numerals. The distal extremity of the catheter apparatus shown in FIG. 8 differs from the apparatus shown in FIG. 1 in that the conducting wires or leads connected to the ultrasonic crystal 52 are connected to the outside world at a point which is proximal of an adapter 122 whereas in the embodiment shown in FIG. 1, the connectors are connected at a point which is distal of the adapters 82 and 88. Thus there is shown an adapter 122 which is provided with an arm 123 through which dye injection and pressure measurements can be made and another fitting 124 which can be utilized in inflating and deflating the balloon 41. Another adapter 126 is provided which is threaded into the proximal end of the adapter 22 and forms a sealing engagement with an O-ring 127 carried by the adapter 122. The torque cable 32 extends through the adapter 126 and is connected to a clutch member 128. The clutch member 128 which carries a finger operated member 129 is adapted to be secured to motorized drive means of the type hereinbefore described for causing rotation of the torque cable 32.

As hereinbefore explained, the conducting wires connected to the ultrasonic crystal 52 are braided into the guide wire 32. Means is carried by the adapter 126 which is adapted to make contact with the conducting wires connected to the crystal 52 and consists of brushes 131 and 132 which are yieldably urged by springs 133 towards the torque cable 32 so as to make contact with the conducting wires or leads carried by the guide wire 32. The springs 133 are held in place by pins 134 which are frictionally seated within the adapter 126. Conducting wires 136 and 137 are connected to the pins 134. These wires 136 and 137 are connected into the system in a manner hereinbefore described with the previous embodiments. The operation of this embodiment is very similar to that described in conjunction with the operation of the embodiment shown in FIG. 1.

Operation of this embodiment of the invention is very similar to that hereinbefore described with the principal advantage being that leads which are connected to the crystal 52 for supplying pulses of energy to the crystal and for receiving signals from the crystal are disposed proximally of the two arm adapter 122.

Still another embodiment of the catheter apparatus of the present invention is shown in FIG. 10. Certain parts of this catheter apparatus 146 are very similar to those hereinbefore described and are identified by the same numbers. Thus there has been provided a housing 27 which has an outwardly facing cutout 28. A coil spring guide wire 36 is secured to the distal extremity of the housing 27 as shown. The balloon 41 is carried by the housing and has its distal extremity secured to the housing by a band 92. The balloon 41 is disposed outside of the housing 27 on the side opposite the cutout 28. A flexible tubular assembly 151 is secured to the proximal end of the housing 27. A three-arm adapter 152 is mounted on the proximal extremity of the tubular assembly 151. The tubular assembly 151 consists of a flexible tubular element 153 formed of a suitable material such as plastic which is provided with a balloon lumen 154 that is in communication with the interior of the balloon 41 and extends into a balloon inflation port 156 provided as a part of the three-arm adapter 152.

A crystal 157 is carried by the housing 27 in a stationary position. As shown, the crystal 157 is mounted vertically or in a direction which is at right angles to the longitudinal axis of the housing 27. It can be mounted in the proximal extremity of the housing 27 in a suitable manner such as by an adhesive. A suitable sound absorbing material 158 is provided behind the ultrasonic crystal 157 and fills the space between the crystal 157 and the distal extremity of the housing 27. A pair of conducting wires 161 are connected to the ultrasonic crystal 157 and extend rearwardly through the housing 27 and are connected into sockets 162 provided in a side arm 163 forming a part of the adapter 152.

The flexible tubular element 153 is provided with a large lumen 163 extending the length thereof and which has a rotatable flexible drive cable 166 disposed therein. The flexible drive cable 166 is formed in the manner hereinbefore described and is secured to a generally cylindrical member 167 which as hereinafter described serves as a reflector mount and also serves to carry the cutter. Thus as shown, the member 167 is provided with a surface 168 which is inclined at an angle of approximately 45° and faces the crystal 157 in such a manner so that sound waves propagated by the crystal impinge upon the surface 168 and are propagated outwardly in a direction substantially at right angles to the longitudinal axis of the housing. Since the reflector surface 168 is provided on the distal end of the member 167, the circular cutting edge 169 is provided on the member 167 at the proximal extremity thereof. A truncated conical recess 171 is provided in the proximal extremity of the member 167. The conical recess 171 can be used as a reservoir for collecting material as it is removed by the circular cutting edge 169.

The three-arm adapter 152 is provided with another arm 173 which serves as an infusion port and which is in communication with the lumen 164 through which the drive cable 166 extends. This lumen 164 opens into the interior of the housing 127 and is in communication with the cutout 28. Another adapter 176 is provided which is threaded into the proximal extremity of the adapter 162 and engages an O-ring 177. The drive cable 166 extends through the adapter 176 and has its distal extremity secured to the clutch member 128. As hereinbefore explained, the clutch member 128 can be secured to a motorized drive means for causing rotational movement of the cutter and mirror member 167.

Operation of the catheter apparatus shown in FIG. 10 may now be described as follows. The operation of this device in many respects is very similar to that hereinbefore described with respect to the placement of the catheter in the vessel. The housing can be positioned in the stenosis hereinbefore described and ultrasonic imaging can be carried out by supplying pulses of electrical energy to the ultrasonic crystal 157 which emanates ultrasonic energy and directs the same onto the 45° reflector 168 which reflects the ultrasonic energy up into the tissue which is immediately opposite the cutout 28. Rotation of the mirror 168 causes an image to be formed which can be viewed in the manner hereinbefore described. This imaging can be carried out by rotating the cable 166 and at the same time advancing the drive cable 166 throughout the length of the cutout 28 to view the stenosis. After the viewing operation has been accomplished and it is ascertained that it is desirable to remove the material creating the stenosis by use of the work performing device in the form of the cutter member 167, the cutter member 167 can be advanced to the distal extremity of the cut-out 28. With the cut-out in the proper location, the balloon 41 can then be inflated through the balloon inflation port 156 to urge the housing 27 in a direction so that the stenosis enters the cutout. As soon as this has been accomplished, the cutter member 157 can be rotated at a high rate of speed and gradually retracted to cause the material forming the stenosis to be removed by the cutter member 157 and collected within the recess 171. This cutting and collecting operation can be continued until the cutter member 167 has been advanced to the extreme proximal position. At this time, the catheter apparatus can be removed and the tissue collected within the recesses 171 can be removed. Thereafter, additional insertions of the catheter apparatus can be made and the same cutting operations performed until the desired amount of material has been removed from the area of the stenosis to provide for increased blood flow through the vessel.

Another embodiment of a catheter apparatus incorporating the present invention is shown in FIG. 11 which is utilized solely for imaging purposes and in which the crystal remains in a fixed longitudinal position. As can be seen from FIG. 11, the catheter apparatus is constructed very similar to the catheter apparatus 180 shown in FIG. 10 with the exception that the cutting mechanism has been eliminated. The use of such a catheter apparatus 180 is desirable where it is unnecessary to provide a cutting function. The catheter apparatus 181 also has many parts which are similar to the catheter apparatus herebefore described. Thus there is provided a housing 181 which carries on its distal extremity a coil spring guide 36. A crystal 182 is provided in the distal extremity of the housing 27 and is disposed vertically or in a direction which is perpendicular to the longitudinal axis of the housing. A sound absorbing backing material 183 is provided in the distal extremity of the housing behind the crystal 182. Conducting wires or leads 184 are connected to the crystal 182. The proximal extremity of the housing 27 is connected to the distal extremity of flexible elongate tubular element 186 which is connected to a two-arm adapter 187. The leads 184 extend through the tubular element 186 and are connected to sockets 188 provided in the arm 189 of the two-arm adapter 187. The tubular element 186 is provided with a large lumen 191 which carries the drive cable 192. The drive cable 192 is connected to a clutch member 193 of the type hereinbefore described which is adapted to be driven by motive means in the manner hereinbefore described. The clutch member 193 is provided with a flange 194 which cooperates with a flange 196 on the adapter 187. The adapter 187 carries an O-ring 197 seated against another flange 198 forming a part of the adapter 187. The O-ring 197 forms a liquid-tight seal with respect to the drive cable 192. The clutch member 193 is thus held in a fixed longitudinal position while still permitting rotation of the same. The adapter 187 is provided with a tapered surface 199 adapted to fit into the motive drive means.

The drive cable 192 has its distal extremity secured to a rotating member 203 which is provided with a surface 204 inclined at an angle of 45° which serves as a reflector for reflecting ultrasonic energy generated by the crystal 182 in a direction which is substantially perpendicular to the longitudinal axis of the housing 27. The rotating member 193 as being rotated by the drive cable 192 remains in a fixed longitudinal position and cannot be advanced or retracted with respect to the ultrasonic crystal 182. The large lumen 191 is in communication with a side arm port 206 which forms a part of the two-arm adapter 187. The housing 181 as shown encloses the surface 204 and thus must be formed of a suitable material which is substantially transparent to ultrasonic energy. Alternatively, if desired, a cutout 207 as shown by the dashed lines can be provided through which the ultrasonic energy can pass.

The operation of the catheter apparatus 180 shown in FIG. 11 is very similar to that hereinbefore described with the exception that the cutting operation is omitted. With this catheter apparatus, the device can be inserted in the same manner as with respect to the other devices hereinbefore described. When the device is in the desired location, as for example, in the stenosis, the stenosis can be imaged ultrasonically by causing the rotating member 203 to be rotated with respect to the crystal 182 to cause ultrasonic energy to be directed upwardly and outwardly through the housing 181 to impinge upon the sidewalls of the vessel in which the catheter apparatus 180 is positioned. If a different longitudinal position is desired to be scanned, the entire catheter apparatus 181 can be shifted longitudinally in the vessel to the desired location. After the ultrasonic imaging has been completed, the catheter apparatus 180 can be removed and other operations performed if desired with other instruments.

It should be appreciated that if desired another embodiment of catheter apparatus used solely for imaging can be provided by mounting the crystal at the end of the torque cable as illustrated in FIG. 8 so that the crystal is rotated about an axis parallel to the longitudinal axis of the housing.

From the foregoing it can be seen that a twodimensional ultrasound image is generated by rotating a crystal or a mirror which is located at the tip of the catheter. Good resolution is obtained because of the relatively high frequency i.e., 5 to 50 megahertz that is used. The image which is created is perpendicular to the longer axis of the catheter. The motor which is utilized for rotating the crystal is external to the patient. Rotation of the crystal is made possible because of the electrical connection made with the brush contacts. The use of the balloon stabilizes the housing so that the cutting operation can be readily accomplished.

The apparatus and system of the present invention makes it possible to obtain images in very small vessels and has made it possible to accomplish the same by utilizing the precision driving of a very flexible cable. The catheter apparatus in addition to being capable of imaging is also capable of being steered by the flexible guide wire secured to the tip.

It is apparent from the foregoing that there has been provided a catheter apparatus, system and method which is particularly useful for intravascular twodimension ultrasonography which can be utilized with many different types of operations, as for example, in performing atherectomies.

What is claimed is:

1. A catheter apparatus for obtaining an image of a patient's vessel having a wall comprising:
    a flexible tubular element adapted for insertion into the body lumen, the tubular element having distal and proximal extremities;
    a housing having distal and proximal ends and a longitudinal axis, the proximal end of the housing being secured to the distal extremity of the tubular element, the housing having a portion thereof that is substantially transparent to ultrasonic energy;
    ultrasonic means for generating ultrasonic signals and directing the ultrasonic signals in a direction that is substantially perpendicular to the longitudinal axis of the housing and for receiving reflections of the signals generated, the ultrasonic means including a rotatable member that is movable longitudinally and rotatably relative to the housing during scanning to permit scanning a discrete length of the vessel wall;
    drive means extending through the tubular element and connected to the rotatable member for causing both longitudinal and rotational movement of the rotatable member with respect to the housing about the longitudinal axis of the housing whereby the ultrasonic signals generated by the ultrasonic means are directed onto the vessel wall and the ultrasonic signals reflected by the vessel wall are received by the ultrasonic means;
    and a cutting element secured to said rotatable member for longitudinal movement relative to the housing, said cutting element having a circular cutting edge lying in a plane which is substantially perpendicular to the longitudinal axis of the housing.

2. Apparatus as in claim 1 together with means carried by the housing for collecting material which is removed by the cutting edge.

3. Apparatus as in claim 1 wherein the cutting element includes a recess formed therein for receiving material removed by the cutting edge.

4. Apparatus as in claim 1 together with flexible guide wire means associated with the housing for facilitating steering of the catheter apparatus.

5. Apparatus as in claim 1 wherein the circular cutting edge faces in a direction towards the distal extremity of the housing.

6. Apparatus as in claim 1 wherein the circular cutting edge faces in a direction toward the proximal extremity of the housing.

7. In a catheter apparatus for obtaining an image of a vessel in the vascular system of a patient, a flexible tubular element adapted to be inserted into the vessel and having a longitudinal axis, a flexible rotatable element disposed within the tubular element for rotational movement about the longitudinal axis relative to the tubular element, an ultrasonic transducer carried by the flexible tubular element for generating and receiving ultrasonic signals, electrical circuit means carried by the tubular element and connected to the transducer for supplying signals to and receiving signals from the transducer, and drive means for imparting longitudinal and rotational movement to the rotatable element and directing means mounted on the rotatable element for causing the ultrasonic signals to be directed outwardly and received inwardly relative to the axis of rotation of the rotatable element during rotational and longitudinal movement of the rotatable element so that the ultrasonic signals are rotated and moved longitudinally to provide an image of the portion of the vessel being veiwed.

8. A catheter apparatus as in claim 7 together with means for displaying an image from the signals received from the transducer during rotating of the rotatable element.

9. A catheter apparatus as in claim 7 wherein said reducing means is a cutting device.

10. A catheter apparatus as in claim 7 wherein said ultrasonic transducer includes a crystal together with a backing material carried by the crystal for inhibiting propagation of sonic waves from the crystal in the direction of the backing material.

11. A catheter apparatus as in claim 7 wherein said circuit means is carried by the tubular element.

12. In a catheter apparatus for obtaining an image of a vessel in the vascular system of a patient, a flexible tubular element adapted to be inserted into the vessel, a flexible rotatable element disposed within the tubular element for rotational movement relative to the tubular element, an ultrasonic transducer carried by the flexible tubular element for generating ultrasonic signals, electrical circuit means carried by the tubular element and connected to the transducer for supplying signals to and receiving signals from the transducer, and drive means for imparting rotational movement to the rotatable element and directing means mounted on the rotatable element for causing the ultrasonic signals to be directed outwardly and received inwardly relative to the axis of rotation of the rotatable element during rotation of the rotatable element to provide information with respect to an image of the portion of the vessel being viewed and reducing means secured to the rotatable element for reducing a stenosis within the vessel, the ultrasonic transducer being disposed in relatively close proximity to the reducing means.

13. A catheter apparatus as in claim 12 together with inflatable balloon carried by the reducing means and adapted to be inflated to stabilize the reducing means, and wherein said tubular element includes means for inflating and deflating the balloon.

14. In a catheter system for obtaining an image of a vessel in a vascular system, an elongate flexible element adapted to enter the vessel, a flexible rotatable elongate element disposed in the tubular element, an ultrasonic transducer carried by the flexible rotatable element and being rotatable therewith for scanning the vessel, motor means for rotating the flexible rotatable element, the flexible rotatable element and the transducer carried thereby being movable longitudinally with respect to the tubular element, transmitter means coupled to the ultrasonic transducer and producing electrical signals and supplying the same to the ultrasonic transducer to cause ultrasonic waves to be propagated therefrom and to be shifted longitudinally as the rotatable element is moved longitudinally and rotated as the rotatable element is rotated, receiver means coupled to the ultrasonic transducer, the ultrasonic transducer being capable of receiving reflected ultrasonic waves and supplying electrical signals to the receiver means, timing control means for causing operation of the transmitter means, the receiver means and the motor means and means connected to the receiver means for creating a visual display of the vessel being scanned by the ultrasonic transducer.

15. A system as in claim 14 together with a work performing device carried by the flexible rotatable element.

16. In a method for obtaining an image of a vessel in the vascular system of a patient using a vascularly interventional catheter having a cutting means for reducing a stenosis within the vessel, and a housing that carries an ultrasonic transducer, introducing the catheter into the vessel, scanning the vessel ultrasonically both rotationally and longitudinally while the cutting means is being operated and creating an image from the scan.

17. A catheter apparatus for obtaining an image of a vascular vessel having a wall comprising:
an elongate flexible tubular element having distal and proximal extremities;
a housing having distal and proximal ends and a longitudinal axis, the proximal end of the housing being secured to the distal extremity of the tubular element, the housing having a portion thereof that is substantially transparent to ultrasonic energy;
ultrasonic means for generating ultrasonic signals and directing the ultrasonic signals in a direction that is substantially perpendicular to the longitudinal axis of the housing and toward the wall of the vessel and for receiving reflections from the walls of the vessel of the ultrasonic signals generated, the ultrasonic means including a rotatable member that is movable longitudinally and rotatably relative to the housing during scanning to permit scanning a discrete length of the vessel; and
motorized drive means extending through the tubular element and connected to the rotatable member and being movable longitudinally and for causing rotational movement of the rotatable member with respect to the housing about the longitudinal axis of the housing so that the ultrasonic signals generated are rotated and can be moved longitudinally with respect to the wall of the vessel.

18. Apparatus as recited in claim 17 wherein said rotatable member carries the ultrasonic transducer.

19. Apparatus as in claim 17 wherein said rotatable member is a reflector inclined at an angle of approximately 45° and wherein the transducer is disposed in a direction which is perpendicular to the longitudinal axis of the housing and is mounted in a fixed position in the housing, whereby ultrasonic energy from the transducer is directed onto the reflector and reflected ultrasonic energy is received by the reflector and directed onto the transducer.

20. Apparatus as in claim 17 wherein the housing is provided with a cutout on one side, together with an inflatable balloon carried by the housing and disposed on the exterior of the housing on the side of the housing opposite the cutout and means carried by the tubular element for inflating and deflating the inflatable balloon.

21. A catheter apparatus for obtaining an image of a vascular vessel having a stenosis therein comprising:
a flexible tubular element adapted for insertion into the vascular vessel, the tubular element having distal and proximal extremities;
a housing having distal and proximal ends and a longitudinal axis, the proximal end of the housing being secured to the distal extremity of the tubular element, the housing having a portion thereof that is substantially transparent to ultrasonic energy;
ultrasonic means for generating ultrasonic signals and directing the ultrasonic signals in a direction that is substantially perpendicular to the longitudinal axis of the housing and for receiving reflections of the signals generated, the ultrasonic means including a rotatable member that is movable longitudinally and rotatably relative to the housing during scanning to permit scanning a discrete length of the vessel;
drive means extending through the tubular element and connected to the rotatable member permitting longitudinal movement and for causing rotational movement of the rotatable member with respect to the housing about the longitudinal axis of the housing so that the ultrasonic signals generated by the ultrasonic means are directed onto the vessel and the ultrasonic signals reflected by the vessel are received by the ultrasonic means; and means coupled to said drive means for removing materials from the stenosis including a cutter having an annular cutting edge.

22. A catheter apparatus for obtaining an image of a vascular vessel having a wall comprising:

a flexible tubular member adapted for insertion into the vascular vessel and having a longitudinal axis, ultrasonic means for generating ultrasonic signals and detecting reflections of the ultrasonic signals, the ultrasonic means including a rotatable element disposed within the tubular member and adapted for rotational and longitudinal movement relative to the longitudinal axis of the tubular member, the rotatable element directing the ultrasonic signals outwardly from the catheter apparatus towards the wall of the vessel, drive means connected to the rotatable element and extending through the tubular member for rotating the rotational element relative to the longitudinal axis of the tubular member, and permitting longitudinal movement of the rotatable element along the longitudinal axis and reducing means carried by the tubular member for reducing a stenosis within the vessel, the reducing means and the ultrasonic means being adapted so that imaging of the vessel can occur simultaneously while reducing the stenosis.

23. In a catheter apparatus for obtaining an image of a vessel in a body and reducing a stenosis within the vessel the vessel having a vessel wall, a flexible tubular element adapted for insertion into the vessel and having a longitudinal axis, a cutter rotatable relative to the tubular element with respect to the longitudinal axis of the tubular element for reducing the stenosis, ultrasonic means for generating ultrasonic signals and detecting reflections of the ultrasonic signals, the ultrasonic means including a rotatable element adapted for rotational movement with the cutter relative to the longitudinal axis of the tubular member for directing the ultrasonic signals outwardly from the catheter apparatus towards the vessel wall, and drive means connected to the cutter and rotatable element and extending through the tubular member for rotating the cutter and rotatable element relative to the tubular member.

24. A catheter apparatus as in claim 23, further comprising a motor means for rotating the drive means.

25. In a catheter apparatus for obtaining an image of the wall of a vessel in the vascular system of a patient, an elongate flexible tubular element having distal and proximal extremities, said distal extremity having a longitudinal axis, flexible guide wire means adapted to extend beyond the distal extremity of the tubular element longitudinally of the longitudinal axis of the distal extremity of the tubular element, the flexible guide wire means and the tubular element being of a size such that they can be readily introduced into the vessel, the tubular element and the flexible guide wire means having a flexibility so that the distal extremity of the tubular element can be advanced in the vessel and follow the path of the vessel, the distal extremity of the tubular element having a portion thereof which is substantially transparent to ultrasonic energy, means including an ultrasonic transducer disposed within the distal extremity of the tubular element for generating ultrasonic energy and for directing the same through said portion toward the wall of the vessel, electrical circuit means connected to the ultrasonic transducer and carried by the tubular element and motor-driven elongate flexible drive means extending through the flexible tubular element and connected to said means for generating and directing ultrasonic energy.

26. A cathether apparatus as in claim 25 wherein said distal extremity of the tubular element is in the form of a housing.

27. A catheter apparatus as in claim 26 wherein the flexible guide wire means is secured to the housing.

28. A catheter apparatus as in claim 25 wherein the means disposed within the tubular element for generating ultrasonic energy and for directing the same also includes a rotatable mirror connected to the flexible drive means.

* * * * *

UNITED STATES PATENT AND TRADEMARK OFFICE
CERTIFICATE OF CORRECTION

PATENT NO. : 4,794,931

DATED : January 3, 1989

INVENTOR(S) : Paul G. Yock

It is certified that error appears in the above—identified patent and that said Letters Patent is hereby corrected as shown below:

Column 11, line 37:
Claim 14, line 2, before "element" please insert --tubular--.

Signed and Sealed this

Fifth Day of January, 1993

Attest:

DOUGLAS B. COMER

Attesting Officer

Acting Commissioner of Patents and Trademarks